(12) United States Patent
Morrow et al.

(10) Patent No.: US 11,391,712 B2
(45) Date of Patent: *Jul. 19, 2022

(54) REMOTE MONITORING OF WATER DISTRIBUTION SYSTEM

(71) Applicant: AMI Investments, LLC, Coppell, TX (US)

(72) Inventors: Brian Morrow, Carrollton, TX (US); Mike Vore, Oskaloosa, IA (US); Charles Kitowski, Colleyville, TX (US); Daniel Copeland, Bessemer, AL (US); Leon G. McCullough, West Des Moines, IA (US)

(73) Assignee: AMI Investments, LLC, Coppell, TX (US)

( * ) Notice: Subject to any disclaimer, the term of this patent is extended or adjusted under 35 U.S.C. 154(b) by 644 days.

This patent is subject to a terminal disclaimer.

(21) Appl. No.: 16/428,585

(22) Filed: May 31, 2019

(65) Prior Publication Data
US 2019/0285604 A1    Sep. 19, 2019

Related U.S. Application Data

(63) Continuation of application No. 15/271,597, filed on Sep. 21, 2016, now Pat. No. 10,317,384.
(Continued)

(51) Int. Cl.
*H04W 4/021* (2018.01)
*G01N 33/18* (2006.01)
(Continued)

(52) U.S. Cl.
CPC ............ *G01N 33/18* (2013.01); *G01L 19/086* (2013.01); *H04W 4/021* (2013.01); *H04W 4/14* (2013.01)

(58) Field of Classification Search
CPC ........ H04W 4/021; H04W 4/14; G01N 33/18; G01L 19/086
(Continued)

(56) References Cited

U.S. PATENT DOCUMENTS 3,585,973 A * 6/1971 Klover .................. F01C 1/3441
123/243
4,055,844 A * 10/1977 Hornbostel, Jr. ....... B60C 23/20
340/591
(Continued)

FOREIGN PATENT DOCUMENTS

AU    2011274272 B2    5/2015
CA    2801242 A1    1/2012
(Continued)

OTHER PUBLICATIONS

Canadian Examination Report dated Dec. 2, 2020.
(Continued)

*Primary Examiner* — Peter J Macchiarolo
*Assistant Examiner* — Mohammed E Keramet-Amircolai
(74) *Attorney, Agent, or Firm* — Maynard, Cooper & Gale, P.C.; Brian Sattizahn

(57) ABSTRACT

A liquid monitoring system includes a remote measurement device located at a location of the fire hydrant that is in contact with water provided by a water main. The remote measurement device has sensors that measure characteristics of the water and a communication interface that transmits measured information to a communication network device that may be located elsewhere on the fire hydrant. The communication network device communicates with a communication network.

24 Claims, 11 Drawing Sheets

Related U.S. Application Data

(60) Provisional application No. 62/221,479, filed on Sep. 21, 2015.

(51) Int. Cl.
*H04W 4/14* (2009.01)
*G01L 19/08* (2006.01)

(58) Field of Classification Search
IPC ............ H04W 4/021,4/14; G01N 33/18; G01L 19/086
See application file for complete search history.

(56) References Cited

U.S. PATENT DOCUMENTS

| | | | |
|---|---|---|---|
| 6,058,957 | A | 9/2000 | Honigsbaum |
| 6,442,999 | B1 | 9/2002 | Baumoel |
| 6,624,628 | B1 | 9/2003 | Kwun et al. |
| 6,751,560 | B1 | 6/2004 | Tingley et al. |
| 6,782,751 | B2 | 8/2004 | Linares et al. |
| 6,848,313 | B2 | 2/2005 | Krieg et al. |
| 6,931,445 | B2 | 8/2005 | Davis |
| 6,957,157 | B2 | 10/2005 | Lander |
| 7,111,817 | B2 | 9/2006 | Teti et al. |
| 7,171,854 | B2 | 2/2007 | Nagashima et al. |
| 7,228,726 | B2 | 6/2007 | Kates |
| 7,231,331 | B2 | 6/2007 | Davis |
| 7,266,992 | B2 | 9/2007 | Shamout et al. |
| 7,274,996 | B2 | 9/2007 | Lapinski et al. |
| 7,418,354 | B1 | 8/2008 | Greenlee et al. |
| 7,596,458 | B2 | 9/2009 | Lander |
| 7,607,351 | B2 | 10/2009 | Allison et al. |
| 7,668,670 | B2 | 2/2010 | Lander |
| 7,680,625 | B2 | 3/2010 | Throwbridge et al. |
| 7,711,217 | B2 | 5/2010 | Takahashi et al. |
| 7,740,024 | B2 | 6/2010 | Brodeur et al. |
| 7,746,246 | B2 | 6/2010 | Salser, Jr. |
| 7,837,063 | B2 | 11/2010 | Stoddard |
| 7,980,317 | B1 | 7/2011 | Preta et al. |
| 7,983,869 | B1 | 7/2011 | Hurley |
| 8,109,131 | B2 | 2/2012 | Winter |
| 8,362,919 | B2 | 1/2013 | Cooper et al. |
| 8,401,811 | B1 | 3/2013 | Hurley |
| 8,589,092 | B2 | 11/2013 | Plouffe et al. |
| 8,620,602 | B2 | 12/2013 | Alonso |
| 8,657,021 | B1 | 2/2014 | Preta et al. |
| 8,701,709 | B2 | 4/2014 | Athanasiades et al. |
| 8,805,633 | B1 | 8/2014 | Hurley |
| 8,931,505 | B2 | 1/2015 | Hyland et al. |
| 8,942,947 | B1 | 1/2015 | Hurley |
| 8,997,777 | B2 | 4/2015 | Montague |
| 9,467,754 | B1* | 10/2016 | Sparks .................. H04W 4/12 |
| 9,506,785 | B2 | 11/2016 | Turk |
| 9,596,293 | B2 | 3/2017 | Hirano |
| 9,670,650 | B2 | 6/2017 | Pinney et al. |
| 10,317,384 | B2 | 6/2019 | Morrow et al. |
| 2002/0023220 | A1* | 2/2002 | Kaplan ................. H04L 9/3247 713/176 |
| 2002/0124633 | A1 | 9/2002 | Yang et al. |
| 2007/0120664 | A1 | 5/2007 | Bilbrey |
| 2007/0163334 | A1* | 7/2007 | Boyd .................. G01N 1/2035 73/756 |
| 2008/0189056 | A1 | 8/2008 | Heidl et al. |
| 2008/0281534 | A1 | 11/2008 | Hurley |
| 2008/0289402 | A1* | 11/2008 | Chowdhury ............ C02F 1/008 73/61.71 |
| 2009/0066524 | A1 | 3/2009 | Yukawa et al. |
| 2009/0269140 | A1* | 10/2009 | Hater ...................... B09B 1/00 405/129.95 |
| 2010/0065287 | A1* | 3/2010 | Burkhart ................ A62C 35/68 169/17 |
| 2010/0126601 | A1 | 5/2010 | Heron |
| 2010/0189887 | A1 | 7/2010 | Nielsen |
| 2010/0295672 | A1* | 11/2010 | Hyland .................. G08C 17/02 340/539.1 |
| 2010/0310385 | A1 | 12/2010 | Denne |
| 2011/0094758 | A1* | 4/2011 | Burkhart ................ A62C 35/68 169/17 |
| 2011/0247416 | A1 | 10/2011 | Cooper et al. |
| 2011/0308638 | A1 | 12/2011 | Hyland et al. |
| 2012/0004866 | A1 | 1/2012 | Plouffe et al. |
| 2012/0007743 | A1 | 1/2012 | Solomon |
| 2012/0007744 | A1 | 1/2012 | Pal et al. |
| 2013/0048318 | A1 | 2/2013 | Ewers |
| 2013/0054121 | A1* | 2/2013 | Casoni ................. F02M 35/162 29/888.011 |
| 2013/0138396 | A1 | 5/2013 | Hauffen et al. |
| 2013/0199625 | A1 | 8/2013 | Fleury |
| 2013/0206241 | A1* | 8/2013 | Fleury, Jr. .................. E03B 9/02 137/291 |
| 2013/0314239 | A1 | 11/2013 | Clark |
| 2014/0150554 | A1 | 6/2014 | Rada et al. |
| 2014/0165731 | A1 | 6/2014 | Linford |
| 2014/0224026 | A1 | 8/2014 | Linford et al. |
| 2014/0311587 | A1 | 10/2014 | Ellis |
| 2014/0338464 | A1 | 11/2014 | Ball et al. |
| 2014/0340238 | A1 | 11/2014 | Hyland et al. |
| 2015/0082868 | A1 | 3/2015 | Hyland et al. |
| 2015/0241402 | A1* | 8/2015 | Dooley .................. G01N 33/18 73/61.41 |
| 2016/0097746 | A1 | 4/2016 | Traub |
| 2016/0356755 | A1 | 12/2016 | Gifford et al. |
| 2017/0082592 | A1* | 3/2017 | Morrow ................. G01N 33/18 |
| 2017/0130431 | A1 | 5/2017 | Pinney et al. |
| 2017/0216645 | A1* | 8/2017 | Silvers .................... H04W 4/38 |
| 2017/0234712 | A1 | 8/2017 | Ball et al. |
| 2017/0291141 | A1 | 10/2017 | Dunham |
| 2018/0093117 | A1 | 4/2018 | Hyland et al. |
| 2018/0320828 | A1 | 11/2018 | Lander et al. |
| 2019/0316983 | A1 | 10/2019 | Fleury, Jr. et al. |
| 2020/0088706 | A1 | 3/2020 | Morrow et al. |

FOREIGN PATENT DOCUMENTS

| | | |
|---|---|---|
| CA | 2801242 C | 5/2014 |
| EP | 2735783 A1 | 5/2014 |
| WO | 2012000088 A1 | 1/2012 |
| WO | 2014189901 A1 | 11/2014 |
| WO | 2017175136 A1 | 10/2017 |

OTHER PUBLICATIONS

International Patent Application No. PCT/US2016/052840, "International Preliminary Report on Patentability," dated Apr. 5, 2018.
Canadian Examination Report dated Feb. 28, 2020.
The International Search Report for PCT/US20/49388 dated Dec. 8, 2020.

* cited by examiner

REMOTE MONITORING OF WATER DISTRIBUTION SYSTEM

CROSS-REFERENCE TO RELATED APPLICATIONS

This application is a continuation of U.S. application Ser. No. 15/271,597, entitled "Remote Monitoring of Water Distribution System," filed Sep. 21, 2016, which claims the benefit of U.S. Provisional Application No. 62/221,479, entitled "Remote Monitoring of Water Distribution System," filed Sep. 21, 2015, both of which applications are hereby incorporated by reference in their entirety.

BACKGROUND

Water distribution systems provide water to homes and businesses within a geographic area. The water is treated by a water treatment system prior to distribution in order to ensure that it complies with legal, regulatory, and customer requirements relating to the quality and content of the distributed water. For example, some legal or regulatory requirements may relate to the maximum content of certain chemicals or materials within the water. Customer requirements may not be legally enforced but may nonetheless be related to the desirable taste, smell, and appearance of the water that is distributed to customers who are served by the water distribution system.

A water distribution system may cover a large geographic area. Leaks or blockages within the system may result in a reduced level of service provided to customers and loss of valuable water resources. In some cases, undesirable chemicals or materials could be introduced to the water distribution system after the water leaves the treatment facility, at some intermediate locations within the water distribution system. The water mains that distribute water within the water distribution system are located underground, and are therefore difficult to access or monitor.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

A water distribution system has a water treatment facility that supplies water to an area such as a municipality, industrial park, commercial area, mixed use area or development, and various other locations and environments. The water is distributed through water mains, and fire hydrants are located throughout the water distribution system. These fire hydrants may be dry-barrel hydrant or wet-barrel hydrants. Whatever the manner of construction, the hydrant includes a valve that can be opened in order to provide water from the water main to nozzles of the hydrant. The water running thought the water main is pressurized, and in this manner, delivers pressurized water to the fire hydrant.

A typical water distribution system may cover a large geographic area. As a result, even though the water that is provided from the water distribution system may be compliant with legal, regulatory, and customer requirements, it is possible that problems with the water may be introduced elsewhere within the water distribution system as a whole. This may result in pressure losses within the water distribution system or the introduction of undesirable chemicals or materials at remote locations within the water distribution system.

The fire hydrants are located throughout the water distribution system, and may provide a location for remote monitoring of conditions of the water distribution system such as water pressure, water quality, chemical content, solid content, or any other suitable characteristics of the water within the water distribution system. A remote measurement device may be located at a location where it is exposed to the water flow of the water distribution system, for example, at a valve of a fire hydrant or as an insert that connects to a flange of the fire hydrant. The remote measurement device may include sensors that measure any suitable characteristics of the water or the water distribution system, such as pressure or characteristics of the water.

The remote measurement device may include a processor that processes the output of the sensors, and in some embodiments, calculates measurement values based on the sensor outputs. The remote measurement device may also include a communication interface that transmits the sensor outputs and other calculated values to a communication network device that is located at the fire hydrant, for example, near the bonnet of the fire hydrant (e.g., within a cap of the fire hydrant). This information may be communicated through either a wired connection or wirelessly. The communication network device of the fire hydrant may communicate this information to a monitoring system of the water distribution system. This information may be used by the monitoring system to identify problems within the water distribution system.

Figure 1:
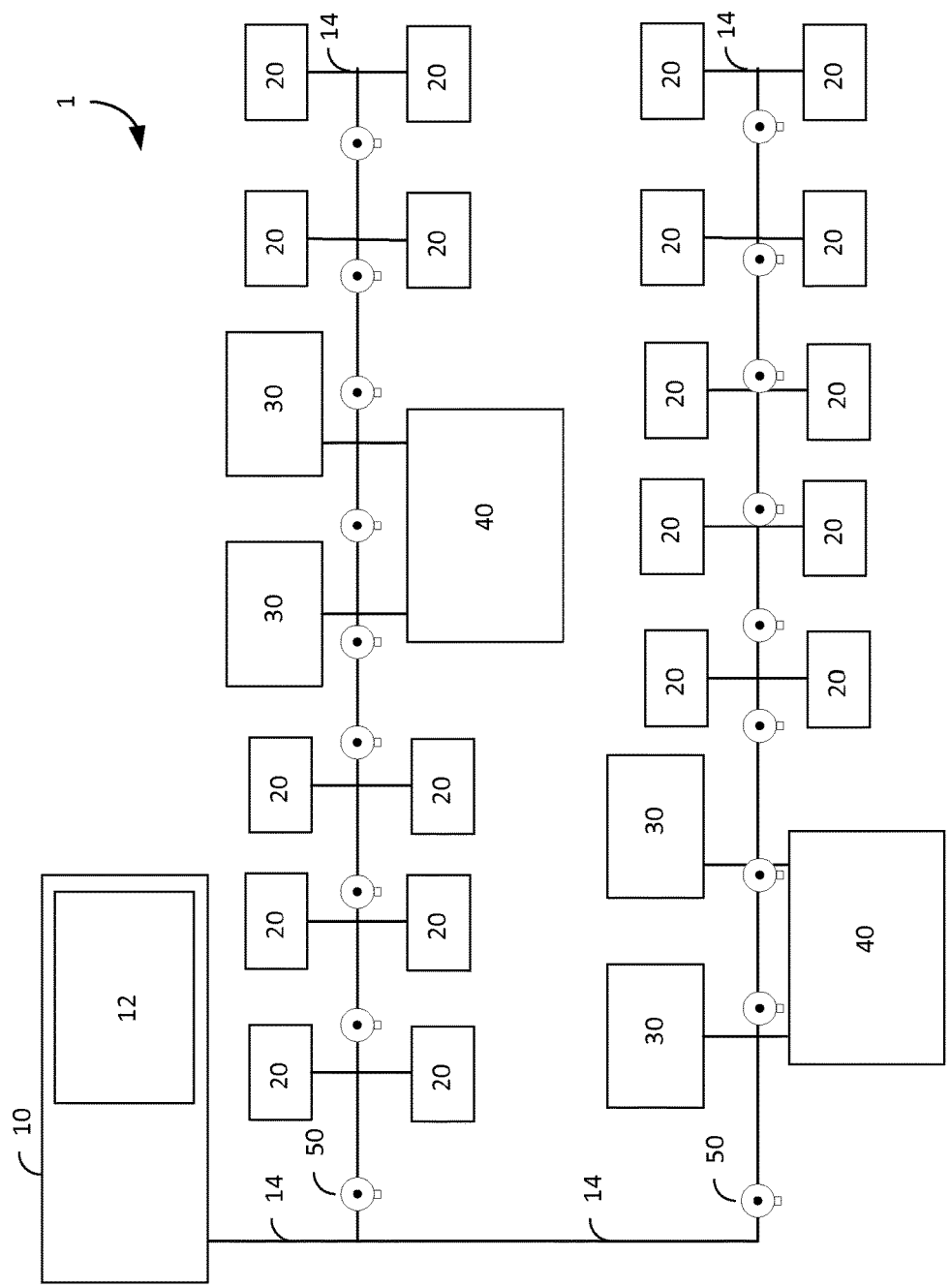
FIG. 1 shows an illustrative water distribution system in accordance with some embodiments of the present disclosure.

FIG. 1 shows an illustrative water distribution system 1 in accordance with some embodiments of the present disclosure. In one embodiment, the water distribution system may include a water treatment facility 10 that includes a central monitoring system 12. Water is provided to the water treatment facility 10 from a water source (not depicted). Water treatment facility 10 treats the water that is provided from the water source such that it complies with legal, regulatory, and customer requirements related to water content and quality. Central monitoring system 12 may receive information from remote measurement devices that are located throughout the water distribution system 1 (e.g., at fire hydrants 50) in order to ensure that water that is delivered to different locations throughout the water distribution system 1 complies with the legal, regulatory, and customer requirements. Based on this information, the central monitoring system 12 may report problems within the water distribution system 1 and suggest corrective action such as needed repairs at a location of the water distribution system 1.

In one embodiment, the central monitoring system 12 may identify locations where there is an unexpected loss of pressure within the water distribution system 1. Based on this information, the location where an inspection or repair needs to be made may be pinpointed accurately. In a similar manner, the central monitoring system 12 may monitor characteristics of the water, such as material or chemical content, at different locations throughout the water distribution system 1. Based on these characteristics, the central monitoring system 12 may identify a location where water quality does not comply with legal, regulatory, or customer requirements. In addition, central monitoring system 12 may monitor aspects of the water distribution system 1 over time, for example, to determine usage patterns or other changes to the water distribution system 1.

The water that is provided by the water treatment facility 10 may be provided to water main(s) 14. The water main(s) 14 may distribute the water to customers such as residential customers 20, business customers 30, and industrial customers 40. In some embodiments (not depicted herein), remote measurement devices may be located at one or more of these customer locations in addition to the fire hydrants 50 or instead of the fire hydrants 50. However, as described in more detail herein, at least some of the remote measurement devices may be located at the fire hydrants 50 of the water distribution system 1. This may provide some advantages, for example, that the party that owns or manages the water distribution system 1 is likely to have access to and at least partial control over the fire hydrants 50 and the operation thereof.

Figure 2:
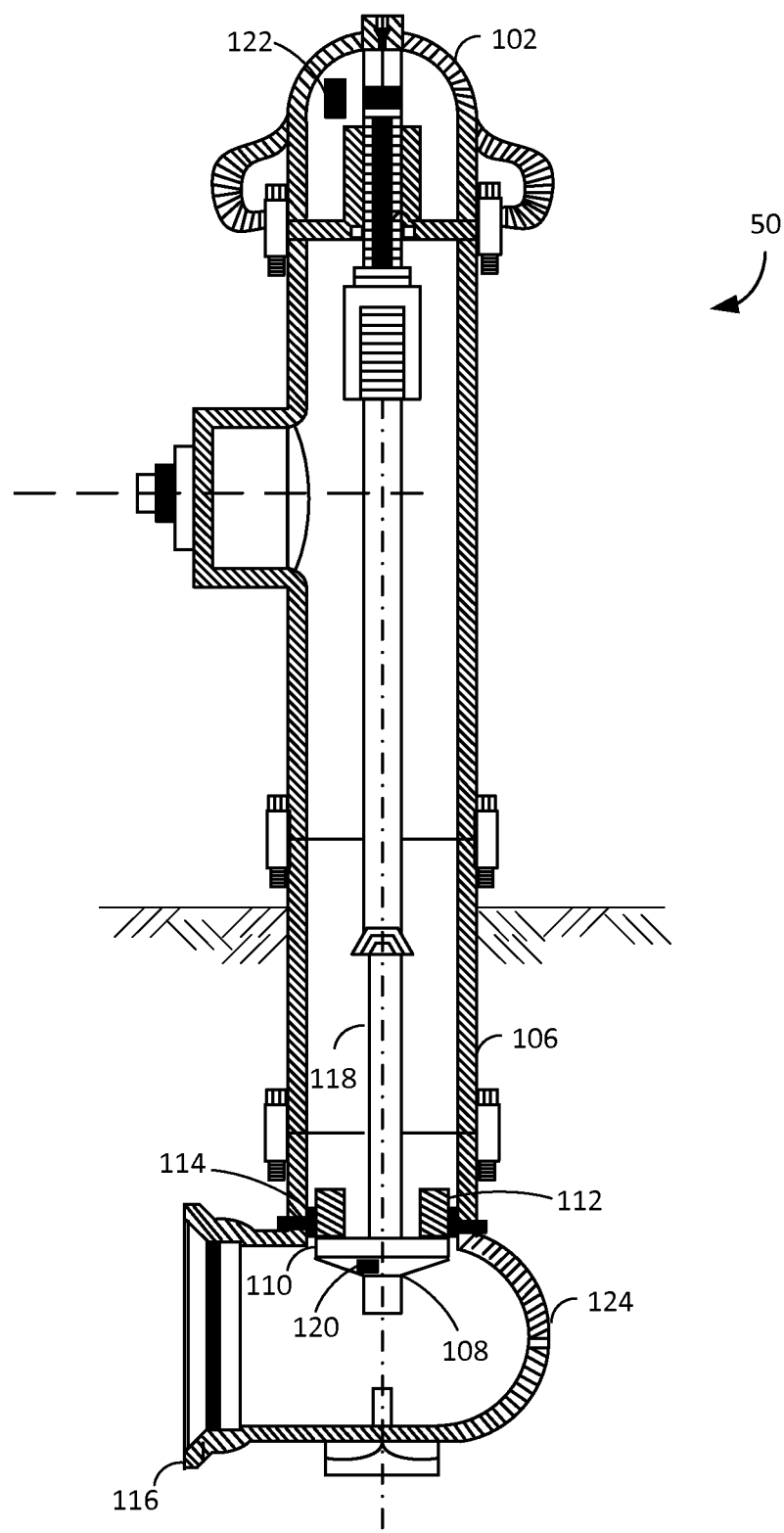
FIG. 2 shows an exemplary fire hydrant including a remote measurement device in accordance with some embodiments of the present disclosure.

FIG. 2 shows an exemplary fire hydrant 50 including a remote measurement device and communication network device in accordance with some embodiments of the present disclosure. Although any suitable type of fire hydrant may be utilized in accordance with the present disclosure (e.g., a dry-barrel or wet-barrel fire hydrant), in one embodiment as depicted in FIG. 2 the fire hydrant 50 may be a dry barrel fire hydrant 50. In one embodiment, the fire hydrant 50 may include a remote measurement device 120 and a communication network device 122. Although certain fire hydrant components will be described in accordance with the present disclosure, it will be understood that the remote measurement device 120 and/or communication network device 122 may be implemented at any suitable location within any suitable fire hydrant 50.

In some embodiments, the fire hydrant 50 may include a shoe 124 that connects to a water main 14 via a flange 116. A valve of the fire hydrant 50 may include a lower valve plate 108 and a valve seat 110. Under normal conditions when water is not being provided to the fire hydrant 50, the lower valve plate 108 may provide a force upon the valve seat 110 such that it creates a seal with seat ring 112 and an upper valve plate (not depicted). A valve stem 118 may be coupled to the lower valve plate 108 such that a user of the fire hydrant may release the seal between the valve seat 110 and the seat ring 112, allowing water from the water main 14 to be provided to the fire hydrant 50 via barrel 106. In some embodiments, seat ring 112 may engage with a drain ring 114, such that the valve stem 118, seat ring 112, and valve (e.g., including lower valve plate 108 and valve seat 110) may be selectively removed and serviced at the fire hydrant 50. In this manner, a remote measurement device 120 may be accessed and serviced as necessary, for example, to replace a battery of remote measurement device 120.

In one embodiment, a remote measurement device 120 may be located in a location that is suitable to measure characteristics of the water that is distributed through the water main 14 of the water distribution system 1. For example, the water main (not depicted in FIG. 2) may be coupled to the shoe 124 via flange 116. Although the remote measurement device 120 may be located in any suitable location that is in contact with the water provided by water main 14 (e.g., at any location of shoe 124), in one embodiment the remote measurement device 120 may be located at an exposed surface of the lower valve plate 108.

Figure 3:
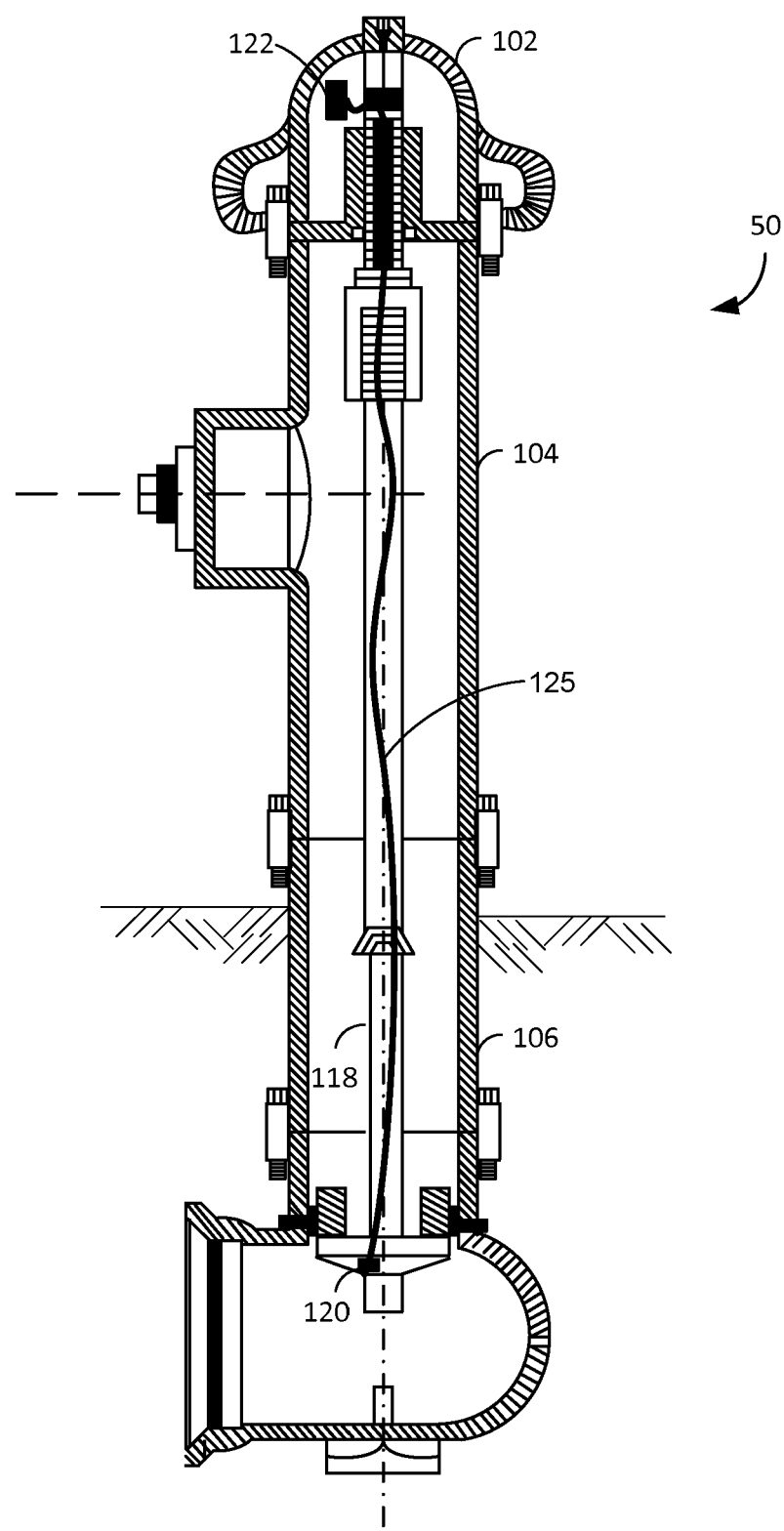
FIG. 3 shows an exemplary fire hydrant including a remote measurement device and valve stem communication path in accordance with some embodiments of the present disclosure.
Figure 4:
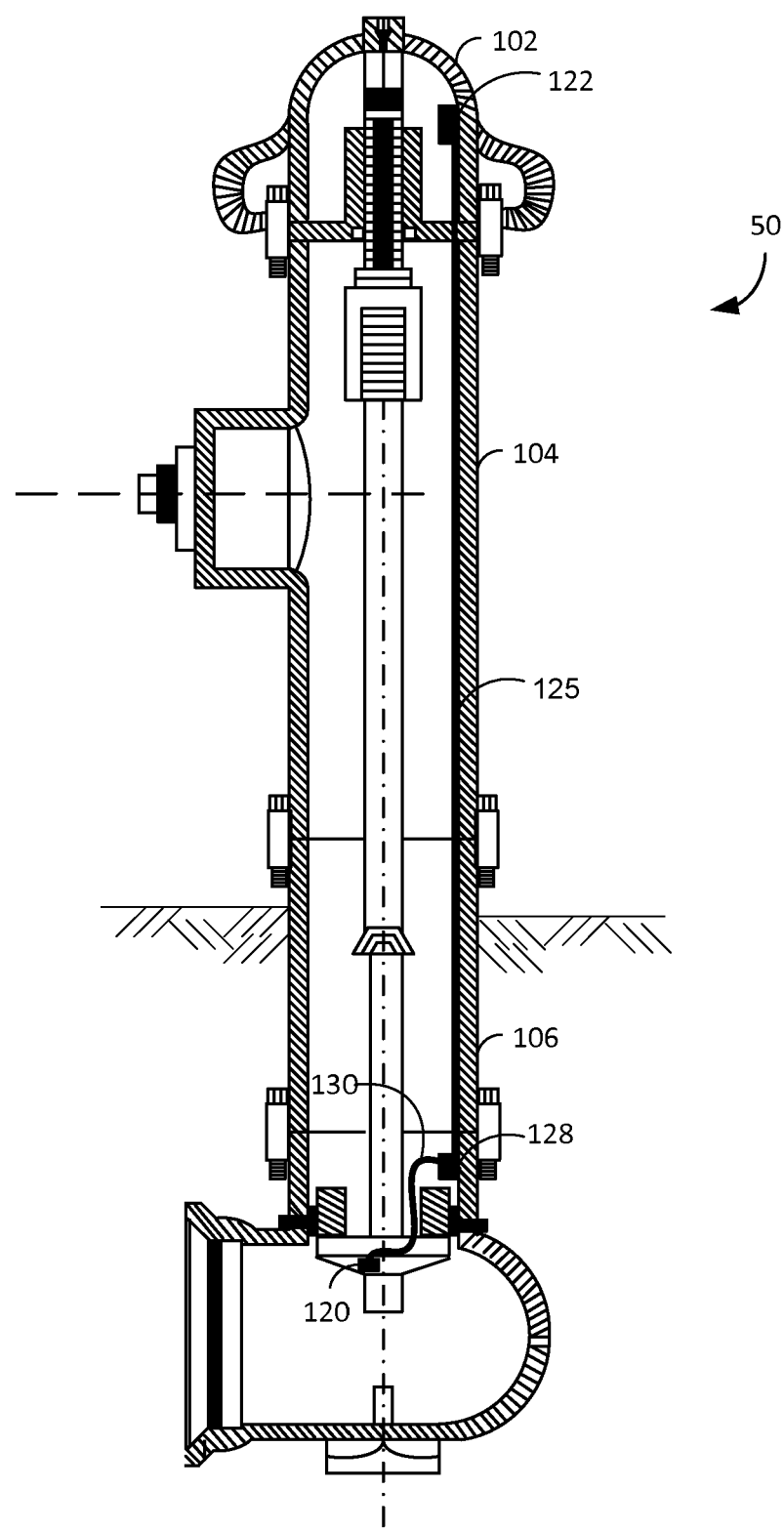
FIG. 4 shows an exemplary fire hydrant including a remote measurement device and barrel communication path in accordance with some embodiments of the present disclosure.

The remote measurement device 120 may include any suitable components to provide for measurement of characteristics of water provided by the water main 14. In one embodiment, the remote measurement device 120 may include a plurality of sensors that measure characteristics of the water such as pressure, turbidity, heave, material content (e.g., total dissolved solids), biological content, chemical content (e.g., chlorine), or any other suitable characteristics. The measured characteristics may be processed at the remote measurement device 120, or some or all of the outputs of the plurality of sensors may be provided to another device (e.g., communication network device 122) for further processing. In some embodiments, the remote measurement device 120 may communicate with the communication network device 122 via a standardized (e.g., WiFi, ZigBee, Bluetooth, Bluetooth low energy, etc.) or proprietary wireless communication protocol operating at frequency such as 900 MHz, 2.4 GHz, or 5.6 GHz. In other embodiments, the remote measurement device 120 may communicate with a communication network device 122 via a wired connection, for example, routed through a cavity of valve stem 118 (e.g., as depicted in FIG. 3) or that is run along an interior surface of barrel 106 (e.g. as depicted in FIG. 4).

In one embodiment, communication network device 122 may be located at a location of fire hydrant 50 that is located above ground, for example, at a location within bonnet 102 of the fire hydrant 50. However, it will be understood that communication network device 122 may be located at any suitable location of fire hydrant 50, including an interior or exterior surface of fire hydrant 50. In addition, in some embodiments, the communication network device 122 and the remote measurement device 120 may be integrated as a single component (e.g., with the communication network device 122 located with remote measurement device 120 at a location that is in contact with water from water main 14, or in a wet-barrel fire hydrant 50).

Communication network device 122 may be in communication with the remote measurement device 120 and may also be in communication with a communication network and/or central monitoring system 12. In some embodiments, communication network device 122 may also be in communication with other communication devices such as network communication devices 122 of other fire hydrants 50 within the water distribution system 1. As described herein, the communication network device 122 may include a wired or wireless communication interface that is compatible with the remote measurement device 120 as well as one or more additional wireless communication interfaces for communicating with the communication network and central monitoring system 122, such as a cellular communication network or mesh communication network. In an exemplary embodiment of a cellular communication network, the communication network device 122 may communicate in any suitable manner, such as via internet protocol data communication or short message system (SMS) messages. In an exemplary embodiment of a mesh communication system, data may be transmitted to the central monitoring system 12 via the mesh network or using a data collection procedure (e.g., using a service vehicle to survey the communication network devices 122 at hydrants 50).

In one embodiment, not depicted herein, rather than providing some or all of the sensors at a location that is in contact with the water passing through the water main 14, it may be possible to provide water to a remote location relative to the water main, for example, using a pitot tube located at the lower valve plate 108, valve seat 110, or shoe 124. Water may be provided via the pitot tube or other similar device such that one or more sensors may be located above ground, for example, directly to network communication device 122 located at a location of bonnet 102.

FIG. 3 shows an exemplary fire hydrant 50 including a remote measurement device 120 and valve stem 118 communication path in accordance with some embodiments of the present disclosure. As is depicted in FIG. 3, a wired connection 125 may be provided between the remote measurement device 120 and the communication network device 122. In the exemplary embodiment of FIG. 3, the wired connection may be located within an interior cavity of the valve stem 118. Although the wired connection 125 may be provided in any suitable manner, in some embodiments, the wired connection may include some slack such that the wired connection is able to accommodate movement of the valve and valve stem 118.

Any suitable signals or combination thereof may be provided via wired connection 125, including but not limited to sensor signals from remote measurement device 120, data signals between remote measurement device 120 and communication network device 122, and power signals provided to remote measurement device 120 and communication network device 122. In one embodiment, remote measurement device 120 may receive power via wired connection 125 and may provide analog or digital signals directly from sensors of remote measurement device 120. In another exemplary embodiment, remote measurement device 120 may process some or all of the signals received at sensors thereof and communicate values determined therefrom to communication network device 122 via a data signal. A data signal may be provided by any suitable standardized or proprietary protocol, such as USB, I²C, GPIO, SPI, or Firewire.

FIG. 4 depicts an exemplary fire hydrant 50 including a remote measurement device 122 and barrel 106 communication path in accordance with some embodiments of the present disclosure. As described for FIG. 3, the communication path depicted in FIG. 4 may include a wired connection 125 between remote measurement device 120 and communication network device 122. As depicted in FIG. 4, the wired connection 125 may be routed along an interior surface of barrel 106. The wired connection may be coupled along the interior surface in any suitable manner, for example, via a channel provided within the interior surface of the fire hydrant 50. In one embodiment, a coupling 128 and connecting wire 130 may be provided at a location relative to the valve (e.g., in an embodiment wherein the remote measurement device 120 is located at the valve) and may allow for the connecting wire 130 to extend along with movements of the valve.

Figure 5:
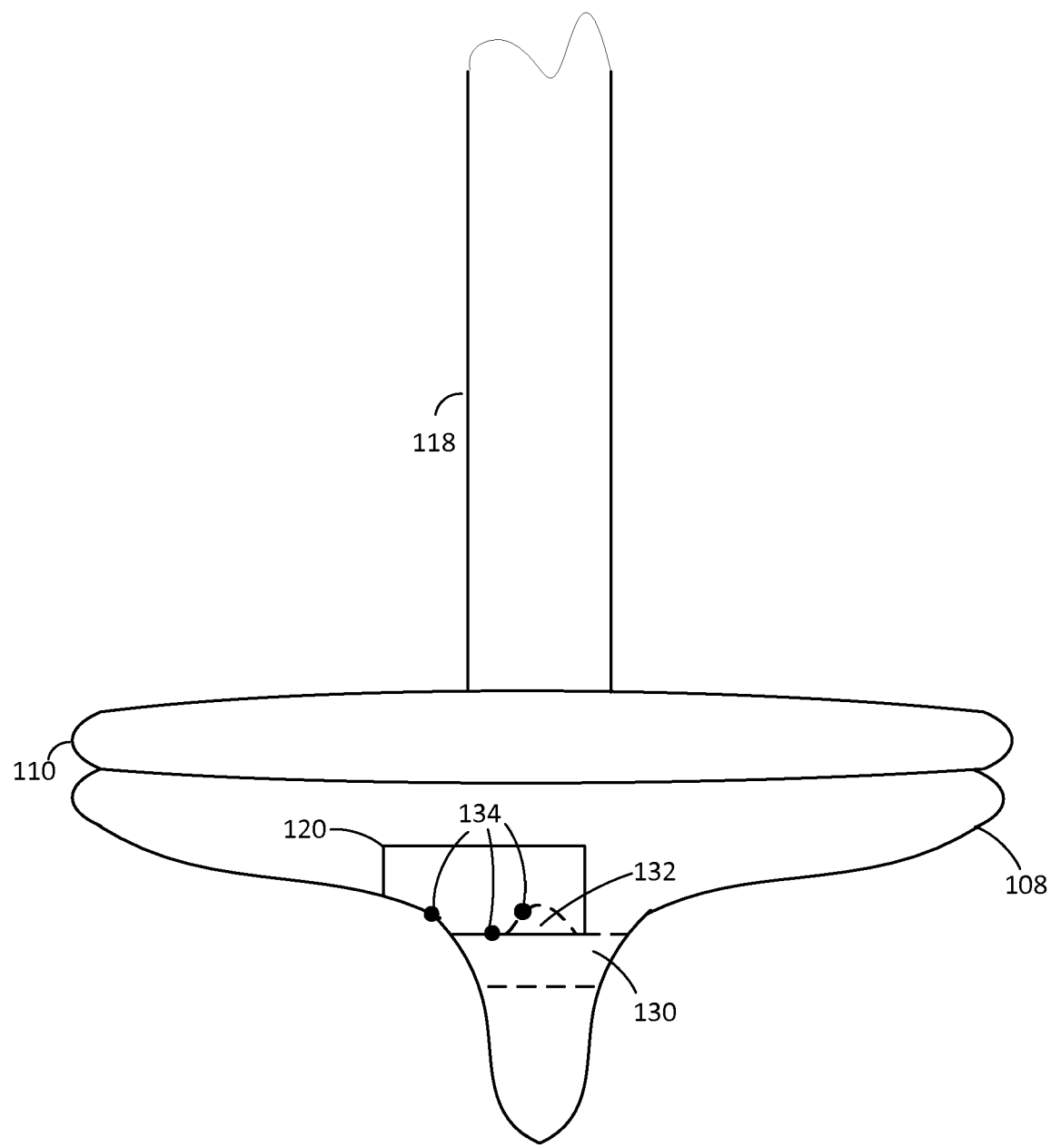
FIG. 5 shows an exemplary remote measurement device located within a cavity of a lower valve plate of a fire hydrant in accordance with some embodiments of the present disclosure.

FIG. 5 shows an exemplary remote measurement device 120 located within a cavity of a lower valve plate 108 of a fire hydrant 50 in accordance with some embodiments of the present disclosure. As described herein, a remote measurement device may be integrated into any suitable component of a fire hydrant that is in contact with water supplied by a water main 14. In one embodiment, the remote measurement device 120 may be integral to the lower valve plate 108 (e.g., located within a cavity of the lower valve plate 108). The lower valve plate may have a sealing surface that creates a seal with the valve seat 110 and an exposed surface located opposite the sealing surface.

Remote measurement device 120 may include sensors 134 that may determine characteristics of the water of water main 14. Examples of sensors may include sensors for pressure, turbidity, heave, material content (e.g., total dissolved solids), biological content, chemical content (e.g., chlorine), or any other suitable characteristics. Sensors may include electrical sensors, mechanical sensors, electromechanical sensors, optical sensors, acoustic sensors, any other suitable sensors, or any combination thereof.

In some embodiments, sensors 134 may be provided at a variety of locations of lower valve plate 108 or another similar component. As depicted in FIG. 5, sensors 134 may be provided at an exterior surface of lower valve plate 108. In some embodiments, a channel 130 may be provided through lower valve plate 108. As depicted in FIG. 5, a sensor 134 may be located at the surface of channel 130, or in some embodiments, within channel 130. A reservoir 132 may also be provided within lower valve plate 108, and one or more sensors 134 may be provided within reservoir 132. In some embodiments, the sensor located at or in the channel 130 or reservoir 132 may include a liquid sampling device that is configured to acquire a sample of the liquid and to determine the one or more characteristics based on the sample.

Figure 6:
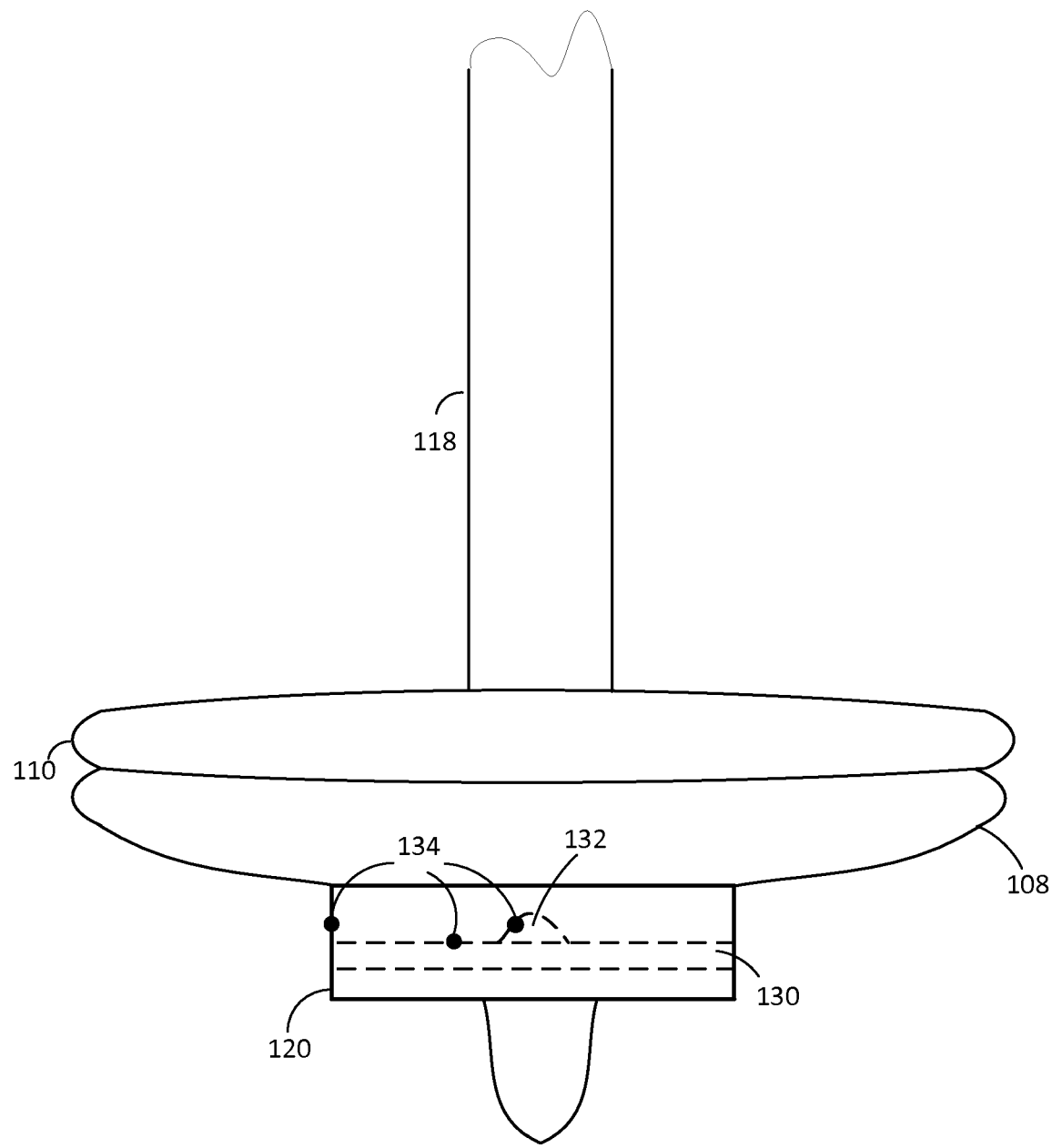
FIG. 6 shows an exemplary remote measurement device located at an exterior surface of a lower valve plate of a fire hydrant in accordance with some embodiments of the present disclosure.

FIG. 6 shows an exemplary remote measurement 120 device located at an exterior surface of a lower valve plate 108 of a fire hydrant 50 in accordance with some embodiments of the present disclosure. As described herein, a remote measurement device may be located at an exterior surface of any suitable component of a fire hydrant 50 that is in contact with water supplied by a water main 14. In one embodiment, the remote measurement device 120 may be fixedly attached to the lower valve plate 108 (e.g., via a weld, bolt, or any other suitable attachment mechanism). The lower valve plate 108 may have a sealing surface that creates a seal with the valve seat 110 and an exposed surface located opposite the sealing surface, to which the remote measurement device is attached.

Similar to FIG. 5, remote measurement device 120 may include sensors 134 that may determine characteristics of the water of water main 14. Examples of sensors may include sensors for pressure, turbidity, heave, material content (e.g., total dissolved solids), biological content, chemical content (e.g., chlorine), or any other suitable characteristics. Sensors may include electrical sensors, mechanical sensors, electro-mechanical sensors, optical sensors, acoustic sensors, any other suitable sensors, or any combination thereof.

In some embodiments, sensors 134 may be provided at a variety of locations of the remote measurement device 120. Sensors 134 may be provided at an exterior surface of remote measurement device 120, at or within a channel 130 of remote measurement device 120, and/or at or within a reservoir 132 of remote measurement device 120.

Figure 7A:
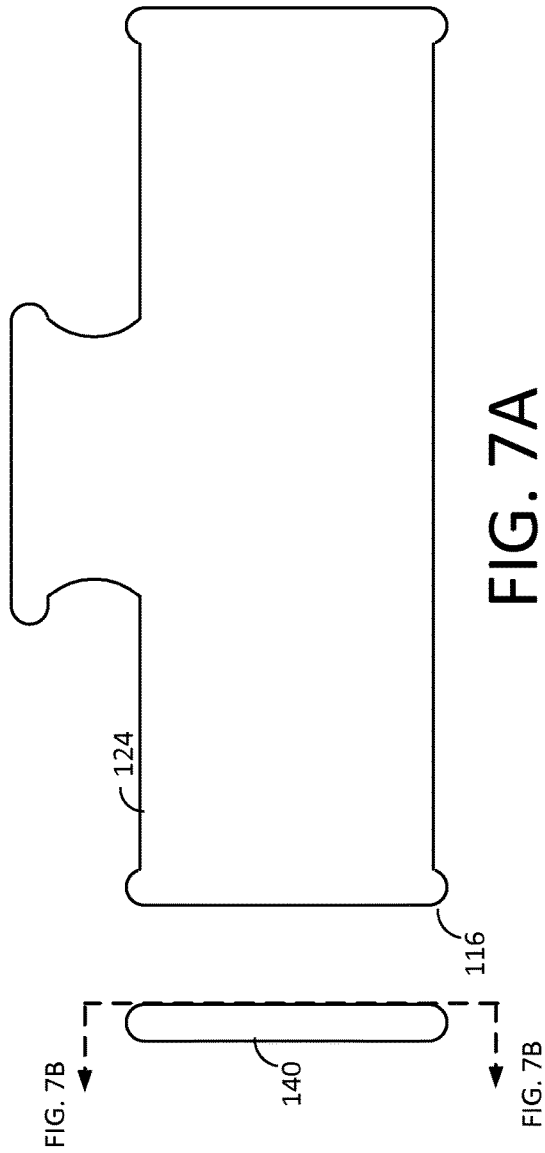
FIG. 7A shows an exemplary embodiment of a remote measurement device located within a flange insert in accordance with some embodiments of the present disclosure.

FIG. 7A shows an exemplary embodiment of a remote measurement device 120 located within a flange insert 140 in accordance with some embodiments of the present disclosure. As described herein, a fire hydrant may include a shoe 124 having a flange 116 that attaches to a water main 14. In one embodiment, a flange insert may be provided that includes the remote measurement device 120. The flange insert 140 may be located between flange 116 and the water main 14, and may be fixedly attached to both in any suitable manner (e.g., bolts and nuts (not depicted)). In a similar manner as is described and depicted for the remote measurement device 120 of FIGS. 2-6, a remote measurement device 120 located at a flange insert 140 may communicate with a communication network device 122 via a wired or wireless connection. In the exemplary embodiment of a wired connection 125, the wired connection 125 may be provided at an interior or exterior surface of the fire hydrant 50.

Figure 7B:
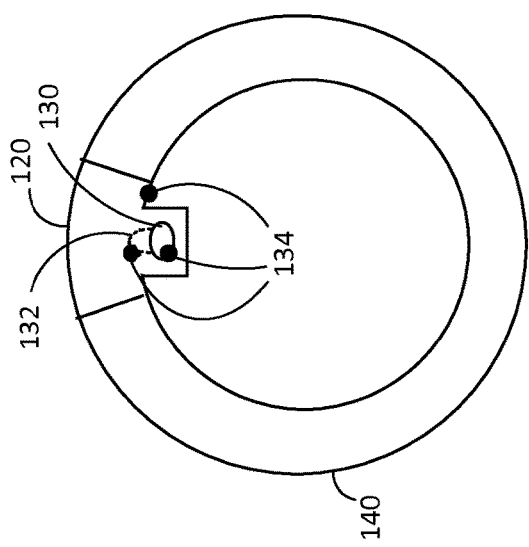
FIG. 7B depicts a perspective view of the flange insert in accordance with some embodiments of the present disclosure.

FIG. 7B depicts a perspective view of the flange insert 140 in accordance with some embodiments of the present disclosure. Although a flange insert may be implemented in any suitable manner, in some embodiments the flange insert 140 may include a remote measurement device 120 located within a portion thereof. As described herein for the remote measurement device 120 of FIGS. 5-6 and depicted in FIG. 7B, sensors 134 may be provided at an exterior surface of remote measurement device 120, at or within a channel 130 of remote measurement device 120, and/or at or within a reservoir 132 of remote measurement device 120.

Figure 8:
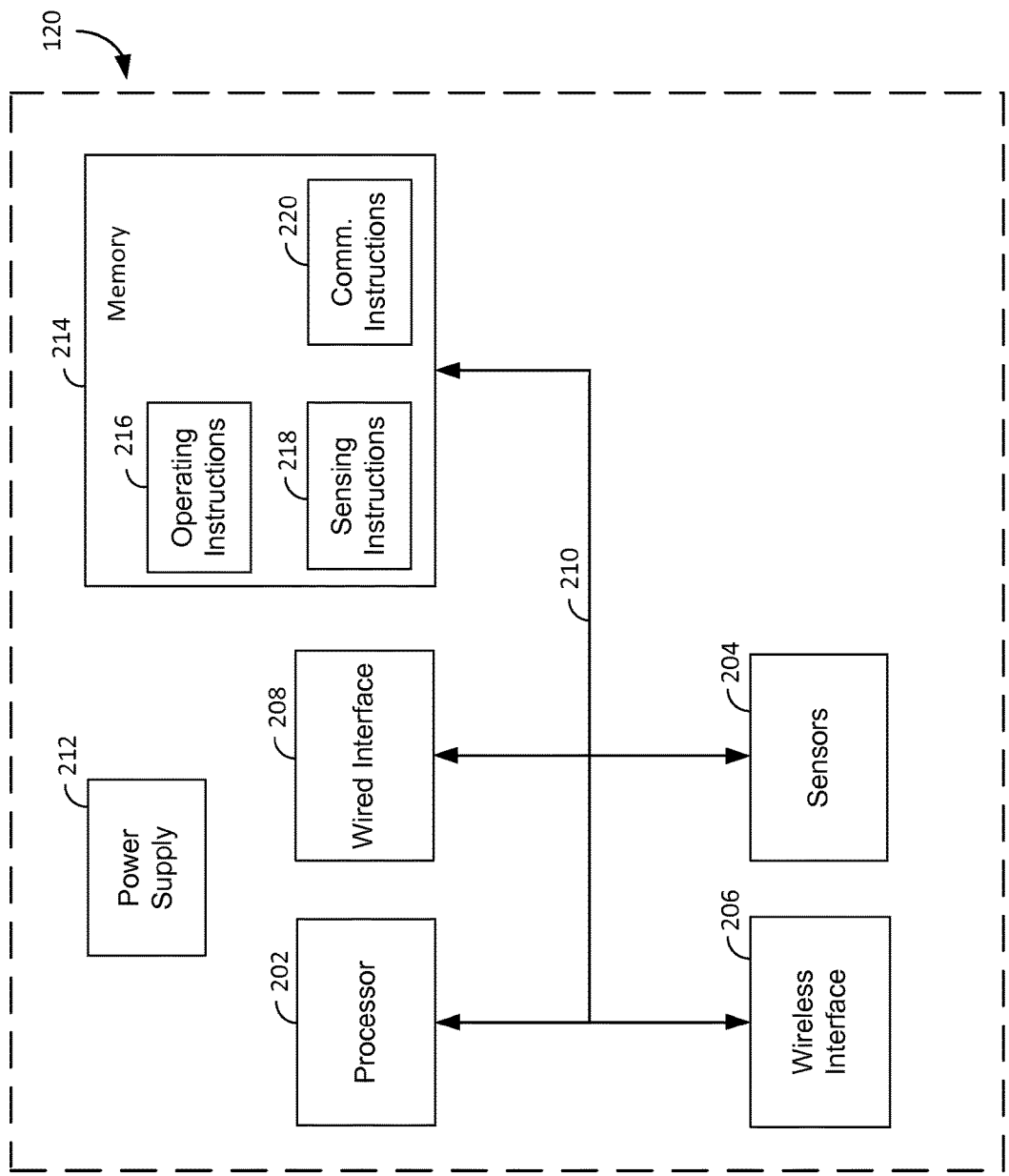
FIG. 8 shows an exemplary remote measurement device in accordance with some embodiments of the present disclosure.

FIG. 8 depicts an exemplary remote measurement device 120 in accordance with some embodiments of the present disclosure. Although remote measurement device 120 may include any suitable components, in one embodiment remote measurement device 120 may include a processor 202, sensors 204, a wireless interface 206, a wired interface 208, internal communication interface 210, a power supply 212, and a memory 214.

Processor 202 may control the operations of the other components of remote measurement device 120, and may include any suitable processor. As described herein, a processor 202 may include any suitable processing device such as a general purpose processor or microprocessor executing instructions from memory, hardware implementations of processing operations (e.g., hardware implementing instructions provided by a hardware description language), any other suitable processor, or any combination thereof. In one embodiment, processor 202 may be a microprocessor that executes instructions stored in memory 214. Memory includes any suitable volatile or non-volatile memory capable of storing information (e.g., instructions and data for the operation and use of remote measurement device 120 and communication network device 122), such as RAM, ROM, EEPROM, flash, magnetic storage, hard drives, any other suitable memory, or any combination thereof.

As described herein, remote measurement device 120 may include sensors 204, which may correspond to the sensors 134 described herein. Remote measurement device may be in communication with sensors 204 via internal communication interface 210. Internal communication interface may include any suitable interfaces for providing signals and data between processor 202 and other components of remote measurement device 120. This may include communication busses such as communication buses such as I$^2$C, SPI, USB, UART, and GPIO. In some embodiments, this may also include connections such that signals from sensors 204 (e.g., measured analog signals) may be provided to processor 202.

Wireless interface 206 may be in communication with processor 202 via the internal communication interface 210, and may provide for wireless communication with other wireless devices such as communication network device 122. Wireless interface 206 may communicate using a standardized (e.g., WiFi, ZigBee, Bluetooth, Bluetooth low energy, etc.) or proprietary wireless communication protocol operating at any suitable frequency such as 900 MHz, 2.4 GHz, or 5.6 GHz. In some embodiments, a suitable wireless communication protocol may be selected or designed for the particular signal path between the remote measurement device 120 and communication network device 122. In an embodiment of a remote measurement device 120 implemented with lower valve plate 108, the wireless communication protocol may be selected based on the material properties of the fire hydrant 50 (e.g., cast iron) and the signal path through the interior cavity of the fire hydrant 50 (including when water is provided to fire hydrant 50). In an embodiment of a remote measurement device 120 implemented with a flange insert 140, the wireless communication protocol may be selected based on the transmission path through the soil to the above-ground portion of the fire hydrant 50

Although in some embodiments a remote measurement device 120 may include both a wireless interface 206 and a wired interface 208, in some embodiments only one of the wireless interface 206 or wired interface 208 may be provided. A wired interface 208 may provide an interface with wired connection 125 in order to allow processor 202 to communicate with communication network device 122 as described herein. The wired connection 208 may be any suitable wired connection to facilitate communication via any suitable protocol, as described herein.

Remote measurement device 120 may also include a power supply 212. Power supply may include a connection to an external power supply (e.g., power supplied by wired connection 125), a battery power source, any other suitable power source, or any combination thereof. In some embodiments, power supply 212 may be a replaceable or rechargeable battery such as lithium-ion, lithium-polymer, nickel-metal hydride, or nickel-cadmium battery. The power supply 212 may provide power to the other components of remote measurement device.

In one embodiment, memory 214 of remote measurement device may include memory for executing instructions with processor 202, memory for storing data, and a plurality of sets of instructions to be run by processor 202. Although memory 214 may include any suitable instructions, in one embodiment the instructions may include operating instructions 216, sensing instructions 218, and communication instructions 220.

Operating instructions 216 may include instructions for controlling the general operations of the remote measurement device 120. In one embodiment, operating instructions may include instructions for an operating system of the remote measurement device 120, and for receiving updates to software, firmware, or configuration parameters of the remote measurement device 120. In one embodiment, remote measurement device 120 may be a battery-powered device that may be in use for long periods of time without being replaced. Operating instructions 216 may include instructions for limiting power consumption of the remote measurement device 120, for example, by periodically placing some of the components of the remote measurement device 120 into a sleep mode. In one embodiment, the sensors 204 and the communication interface (e.g., wireless interface 206 and/or wired interface 208) may be shut off and a majority of the processing operations of the processor 202 may be shut off. In some embodiments, sensing with sensors 204 may only occur on relatively long intervals (e.g., every few minutes) while the processor may check the communication interface (e.g., wireless interface 206 and/or wired interface 208) more frequently to determine whether data has been requested by the communication network device 122. In other embodiments, sensing with sensors may occur more frequently, and the communication interface (e.g., wireless interface 206 and/or wired interface 208) may only be powered on relatively infrequently (e.g., every few hours), or if a warning or error should be provided based on the measurements from the sensors 204.

Sensing instructions 218 may include instructions for operating the sensors 204 and for processing data from the sensors 204. As described herein, sensors 204 may include a variety of types of sensors that measure a variety of different characteristics of the water. Sensing instructions 218 may provide instructions for controlling these sensors, determining values based on signals or data received from the sensors, and performing calculations based on the received signals or data. While in some embodiments, raw sensor data or calculated values may be received or calculated based on the sensing instructions 218, in some embodiments the sensing instructions may also include data analysis such as a comparison with threshold or warning values. For example, if the pressure that is sensed at a pressure sensor of sensors 204 falls below a threshold, sensing instructions 218 may provide for a warning to be provided to communication network device 122. If a chemical or biological content of the water exceeds a threshold parts per million, a warning may be provided to communication network device 122. In some embodiments, sensing instructions may also analyze data trends or perform statistical analysis based on data received from the sensors 204, determine warnings therefrom, and provide the trends, statistics, and/or warnings to the communication network device 122.

Communication instructions 220 may include instructions for communicating with other devices such as communication network device 122. Communications instructions may include instructions for operating the wireless interface 206 and/or wired interface 208, including physical layer, MAC layer, logical link layer, and data link layer instructions to operate the wireless interface 206 and/or wired interface 208 in accordance with a standardized or proprietary communication protocol. Communication instructions 220 may also include instructions for encrypting and decrypting communications between remote measurement device 120 and communication network device 122, such that unauthorized third parties are unable to eavesdrop on such communications. Communication instructions 220 may also include instructions for a message format for communications exchanged between remote measurement device 120 and communication network device 122. The message format may specify message types, such as warning messages, wake up messages, update messages, data upload messages, and data request messages.

Figure 9:
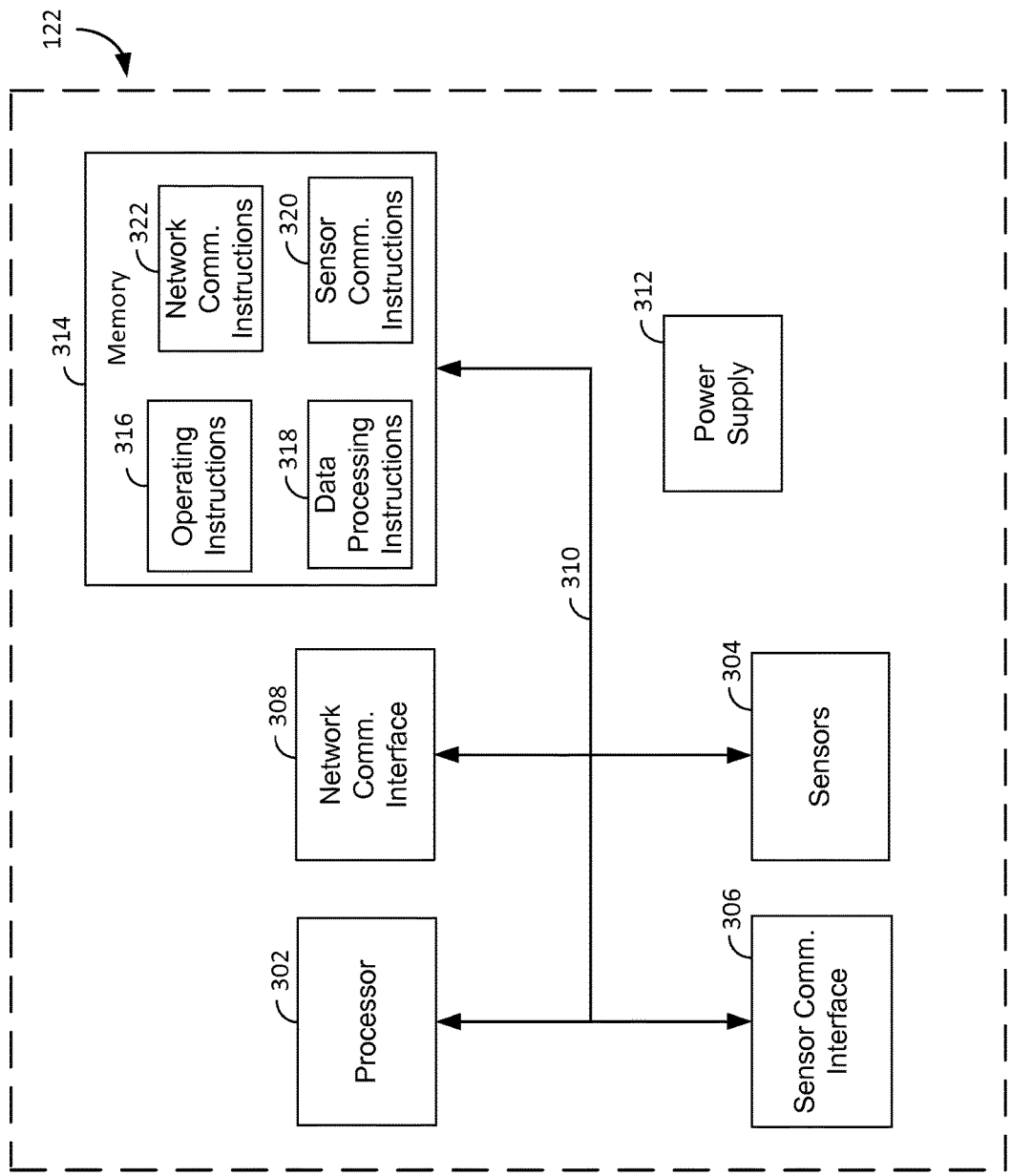
FIG. 9 shows an exemplary communication network device in accordance with some embodiments of the present disclosure.

FIG. 9 shows an exemplary communication network device 122 in accordance with some embodiments of the present disclosure. Although communication network device 122 may include any suitable components, in one embodiment communication network device 122 may include a processor 302, sensors 304, a sensor communication interface 306, a network communication interface 308, internal communication interface 310, power supply 312, and memory 314.

Processor 302 may control the operations of the other components of communication network device 122, and may include any suitable processor. A processor 302 may include any suitable processing device such as a general purpose processor or microprocessor executing instructions from memory, hardware implementations of processing operations (e.g., hardware implementing instructions provided by a hardware description language), any other suitable processor, or any combination thereof. In one embodiment, processor 302 may be a microprocessor that executes instructions stored in memory 314. Memory includes any suitable volatile or non-volatile memory capable of storing information (e.g., instructions and data for the operation and use of communication network device 122), such as RAM, ROM, EEPROM, flash, magnetic storage, hard drives, any other suitable memory, or any combination thereof.

In some embodiments, communication network device 122 may include sensors 204. For example, communication network device 122 may be combined with remote measurement device 120, such that they operate as a single unit. In other embodiments, the sensing operations may be performed directly at network communication device 122, such as when water is provided to communication network device 122 by a pitot tube. In addition, communication network device may sense other characteristics about the location where it is located within fire hydrant 50, such as temperature.

Sensor communication interface 306 may be in communication with processor 302 via the internal communication interface 310, and may provide for wireless or wired communications with remote measurement device 120. In one embodiment, sensor communication interface 306 may include a wireless interface that communicates using a standardized (e.g., WiFi, ZigBee, Bluetooth, Bluetooth low energy, etc.) or proprietary wireless communication protocol operating at any suitable frequency such as 900 MHz, 2.4 GHz, or 5.6 GHz. As described herein, a suitable wireless communication protocol may be selected or designed for the particular signal path between the remote measurement device 120 and communication network device 122. In some embodiments, sensor communication interface may be a wired interface that provides an interface with wired connection 125 in order to allow processor 302 to communicate with remote measurement device 120 as described herein. The wired connection may be any suitable wired connection to facilitate communication via any suitable protocol, as described herein.

Network communication interface 308 may be in communication with a communication network for monitoring characteristics of the water distribution system 1. In one embodiment, the network communication interface 308 may provide for communications with a central monitoring system 12, such as by using a cellular communication network or mesh communication network. In an exemplary embodiment of a cellular communication network, the communication network device 122 may communicate in any suitable manner, such as via internet protocol data communications or short message system (SMS) messages. In an exemplary embodiment of a mesh communication system, data may be transmitted to the central monitoring system 12 via the mesh network or using a data collection procedure (e.g., using a service vehicle to survey the communication network devices 122 at fire hydrants 50).

Communication network device 122 may also include a power supply 312. Power supply 312 may include a connection to an external power supply (e.g., power supplied by a utility system), a battery power source, any other suitable power source, or any combination thereof. In some embodiments, power supply 312 may be a replaceable or rechargeable battery such as lithium-ion, lithium-polymer, nickel-metal hydride, or nickel-cadmium battery. The power supply may provide power to the other components of communication network device 122.

In one embodiment, memory 314 of communication network device 122 may include memory for executing instructions with processor 302, memory for storing data, and a plurality of sets of instructions to be run by processor 302. Although memory 314 may include any suitable instructions, in one embodiment the instructions may include operating instructions 316, data processing instructions 318, sensor communication instructions 320, and network communication instructions 322.

Operating instructions 316 may include instructions for controlling the general operations of the communication network device 122. In one embodiment, operating instructions may include instructions for an operating system of the communication network device 122, and for receiving updates to software, firmware, or configuration parameters of the communication network device 122. In one embodiment, communication network device 122 may be a battery-powered device that may be in use for long periods of time without being replaced. Operating instructions 316 may include instructions for limiting power consumption of the communication network device 122, for example, by periodically placing some of the components of the communication network device 122 into a sleep mode. In one embodiment, the sensors 304 and the communication interfaces (e.g., sensor communication interface 306 and network communication interface 308) may be shut off and a majority of the processing operations of the processor 302 may be shut off. The communication interfaces may wake up on a periodic basis to check for messages from the remote measurement device 120 or the communication network. In some embodiments, the wake up times may be scheduled based on messages from one or more of the central monitoring system 12, remote measurement device 120, and/or communication network device 122. In some embodiments, communication network device 122 may not enter the sleep mode while processing certain information such as warning messages or error messages (e.g., to monitor more frequently based on the occurrence of an error or warning).

Data processing instructions 318 may include instructions for processing data that is received from the remote measurement device 120 via the sensor communication interface 306. As described herein, the sensors of the remote measurement device may measure characteristics such as pressure, turbidity, heave, material content (e.g., total dissolved solids), biological content, chemical content (e.g., chlorine), or any other suitable characteristics. The data processing instructions 318 may process this data to determine warnings, monitor data trends, calculate statistics, or perform any other suitable data processing operations as described herein. In one embodiment, data processing instructions 318 may include instructions for monitoring the change in water pressure over time, and based on identified changes, may provide messages such as warning messages to central monitoring system 12.

Sensor communication instructions 320 may include instructions for communicating with remote measurement device 120. Sensor communications instructions may include instructions for operating the sensor communication interface 306, including physical layer, MAC layer, logical link layer, and data link layer instructions in accordance with a standardized or proprietary communication protocol. Sensor communication instructions 320 may also include instructions for encrypting and decrypting communications between remote measurement device 120 and communication network device 122, such that unauthorized third parties are unable to eavesdrop on such communications. Sensor communication instructions 220 may also include instructions for a message format for communications exchanged between communication network device 120 and communication network device 122. The message format may specify message types, such as warning messages, wake up messages, update messages, data upload messages, and data request messages.

Network communication instructions 322 may include instructions for communicating with a communication network such as a cellular network and/or mesh network. In one embodiment, network communication instructions 322 may include instructions for communicating on a cellular network using an internet protocol data format or a SMS data format. Network communication instructions 322 may also include instructions for communicating using a mesh network (e.g., Zigbee). Communication instructions 320 may also include instructions for encrypting and decrypting communications between communication network device 122 and the communication network, such that unauthorized third parties are unable to eavesdrop on such communications. Communication instructions 320 may also include instructions for a message format for communications exchanged between communication network device 122 and the communications network. The message format may specify message types, such as warning messages, wake up messages, update messages, data upload messages, and data request messages.

Figure 10:
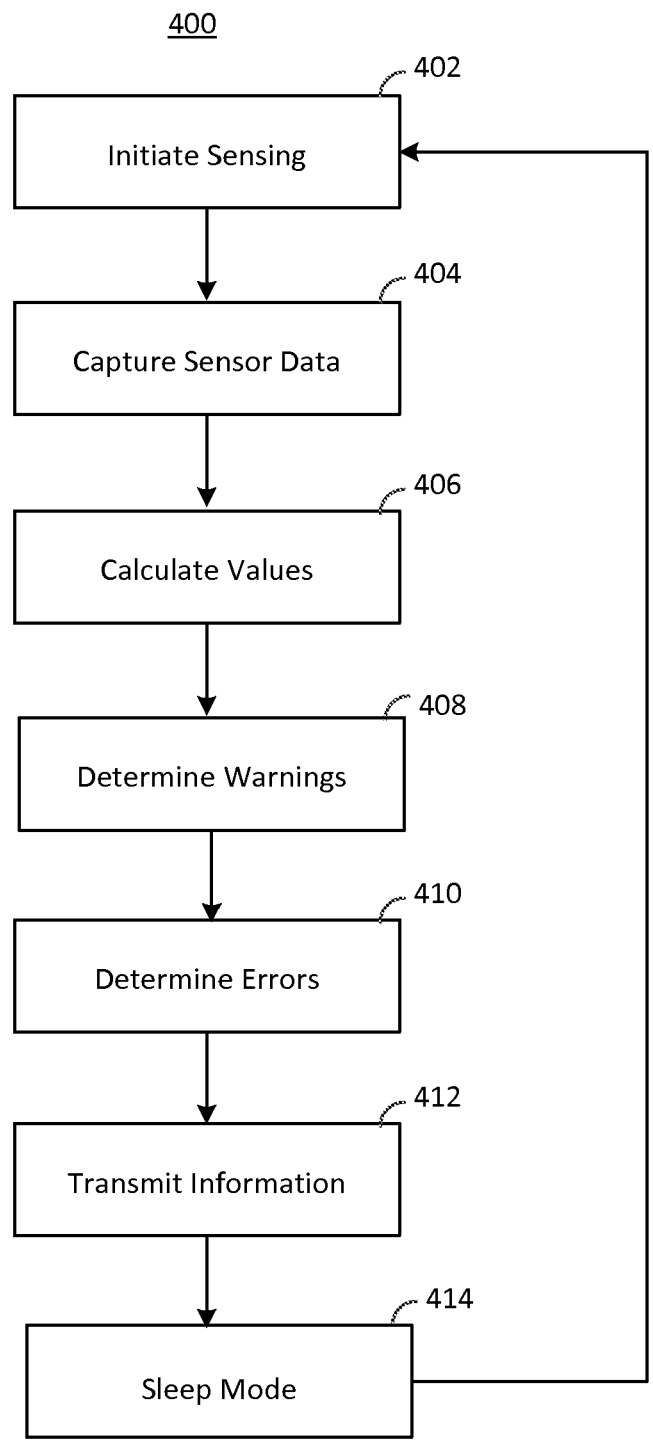
FIG. 10 depicts a non-limiting flow diagram illustrating exemplary methods for operating a remote measurement device in accordance with some embodiments of the present disclosure.

FIG. 10 depicts a non-limiting flow diagram illustrating exemplary methods for operating a remote measurement device 120 in accordance with some embodiments of the present disclosure. Although a particular series of steps 400 are depicted as being performed in a particular order in FIG. 10, it will be understood that one or more steps may be removed or added, and the order of the steps may be modified in any suitable manner. In one embodiment, processing of steps 400 may begin at step 402.

At step 402, remote measurement device 120 may initiate sensing of characteristics of the water flowing through the water main 14. In one embodiment, remote measurement device 120 may be in a sleep mode and may periodically provide power to the sensors. In some embodiments, the sensors may be activated in response to another stimulus such as a message from communication network device 122. Processing may then continue to step 404.

At step 404, remote measurement device 120 may capture sensor data from its sensors. The sensors may be located at the surface of remote measurement device 120, at or in a channel of the remote measurement device 120, at or in a reservoir of the remote measurement device 120, or at any other suitable location. The sensors may provide signals that may be processed by a processor of the remote measurement device (e.g., an analog signal representative of a value of the sensed characteristic) and/or may provide a data signal (e.g., digital data representative of the sensed characteristic). The captured data may be stored in memory of the remote measurement device 120. Processing may continue to step 406.

At step 406, the processor of the remote measurement device 120 may calculate values from the received data. The values may be determined based on applying processing to a received signal (e.g., a received analog signal), based on a received data signal, based on performing calculations relating to a plurality of sensed characteristics, in any other suitable manner, or any combination thereof. In some embodiments, statistics, data trends, and other similar values may also be calculated and stored in memory. Processing may continue to step 408.

At step 408, the processor of the remote measurement device 120 may determine whether there are any warnings associated with the measured data and/or calculated values for the characteristics. Warnings may include conditions that relate to problems with the water distribution system, such as water pressure issues and water quality issues (e.g., turbidity, solid content, chemical content, biological content, etc.). Although warnings may be determined in any suitable manner, in some embodiments the warnings may be based on a comparison of values with thresholds, a rate of change for values, or a combination of values that is indicative of a particular water condition. The warnings may be stored in memory. Once the warnings are determined at step 408, processing may continue to step 410.

At step 410, the processor of the remote measurement device 120 may determine whether there are any errors associated with the measured data and/or calculated values for the characteristics. Errors may relate to the functioning of the remote measurement device (e.g., a failed sensor or low battery) or the fire hydrant (e.g., a failed component such as a seal). Although errors may be determined in any suitable manner, in some embodiments the errors may be determined based on one or more of the measurements or calculated values not being within an acceptable range, or based on a combination of values indicating an error (e.g., a failed seal). The errors may be stored in memory. Once the errors are determined at step 410, processing may continue to step 412.

At step 412, the information that is determined by the remote measurement device (e.g., values for characteristics, warnings, and errors) may be transmitted to another device (e.g., the communication network device 122) via a suitable interface (e.g., a wireless and/or wired interface). In one embodiment, the information may be transmitted during each sensing period that is initiated at step 402. In some embodiments, the information may be transmitted less frequently in the absence of a warning or error. Whether a warning or error is transmitted may also be based on the warning or error type or the severity. Once the information is transmitted, processing may continue to step 414.

At step 414, the remote measurement device 120 may enter a sleep mode. In some embodiments, the parameters for the sleep mode such as sleep time may be based on communications with another device such as the communication network device 122. During the sleep mode, many of the powered components of the remote measurement device 120 such as the sensors and communication interface may not receive power. In some embodiments, certain components (e.g., a pressure sensor) may continue to receive power during the sleep mode in order to determine if there are any critical warnings. Once the sleep mode is entered, processing may return to step 402.

Figure 11:
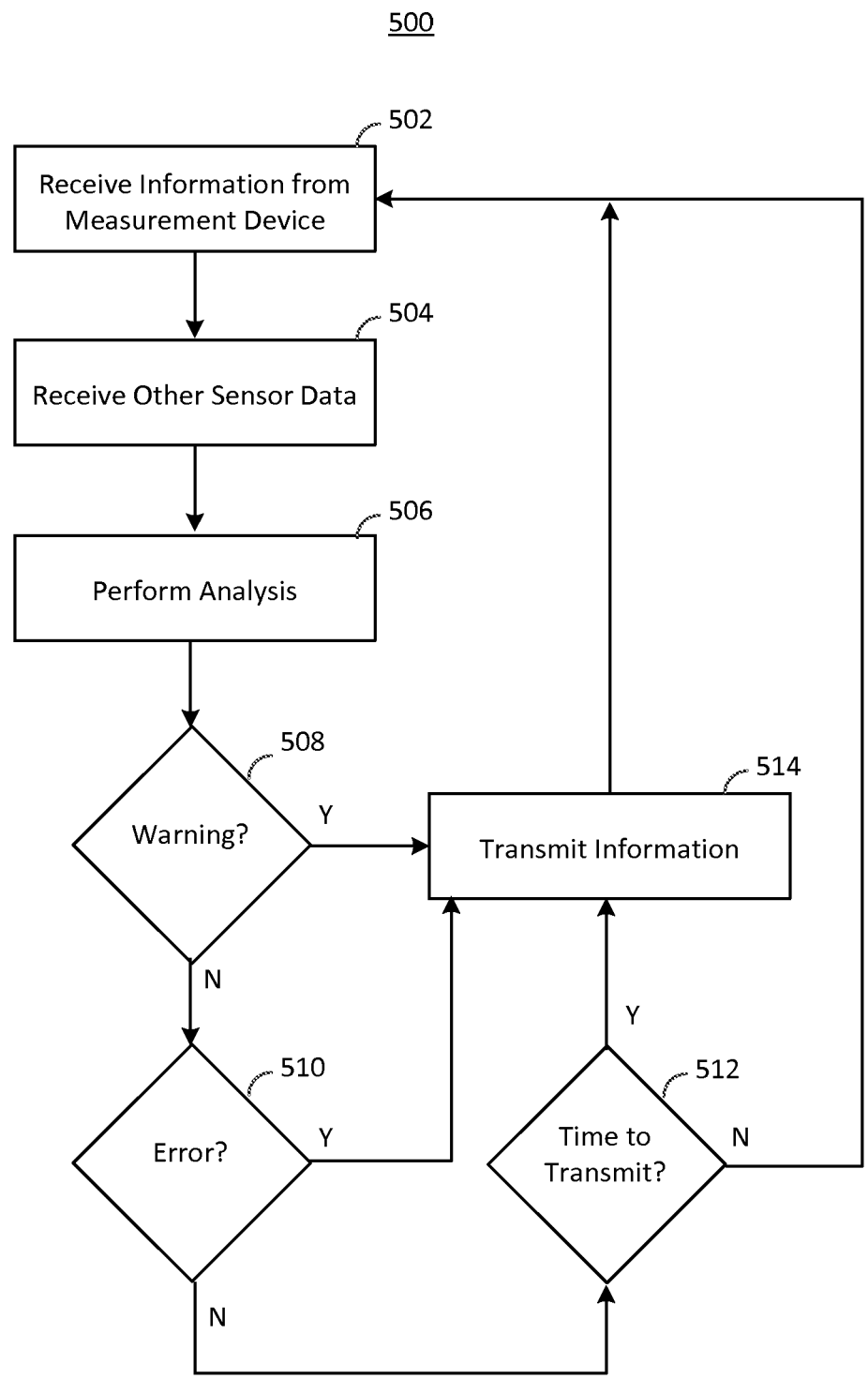
FIG. 11 depicts a non-limiting flow diagram illustrating exemplary methods for operating a communication network device in accordance with some embodiments of the present disclosure.

FIG. 11 depicts a non-limiting flow diagram illustrating exemplary methods for operating a communication network device in accordance with some embodiments of the present disclosure. Although a particular series of steps are depicted as being performed in a particular order in FIG. 11, it will be understood that one or more steps may be removed or added, and the order of the steps may be modified in any suitable manner. In one embodiment, processing of steps 500 may begin at step 502.

At step 502, information may be received at the communication network device 122 via a communication interface in communication with the remote measurement device 122. In some embodiments, the communication network device 122 may be in a sleep mode, and may periodically exit the sleep mode (e.g., at predetermined times) to receive messages from the remote measurement device 120. In other embodiments, the sensor communication interface of the communication network device 122 may remain active, and when a message is received, other circuitry and/or functionality of the communication network device may be enabled. Although not depicted herein, in some embodiments there may be a plurality of remote measurement devices located at different locations within the fire hydrant (e.g., one device located within the path of the water main 14, and another remote measurement device located within a dry barrel of the fire hydrant 50, such that the operation of the valve may be monitored). Once the information has been received at step 502, processing may continue to step 504.

At step 504, the communication network device 122 may receive other sensor data, such as from a local sensor of the communication network device 122. Local sensor data may include any suitable data such as environmental data (e.g., temperature) or data relating to the operation of the communication network device 122. Once the local sensor data has been received at step 504, processing may continue to step 506.

At step 506, the processor of the communication network device 122 may analyze the received information and data to determine data values, warnings, errors, or other suitable values or indications. In some embodiments, the analysis may include the determination of data trends or statistics relating to the received information and values. As described herein, warnings may include conditions that relate to problems with the water distribution system, such as water pressure issues and water quality issues (e.g., turbidity, solid content, chemical content, biological content, etc.), and may be determined in any suitable manner (e.g., based on a comparison of values with thresholds, a rate of change for values, or a combination of values that is indicative of a particular water condition). Errors may relate to the functioning of the remote measurement device 120 or communication network device 122 (e.g., a failed sensor or low battery) or the fire hydrant (e.g., a failed component such as a seal). Although errors may be determined in any suitable manner, in some embodiments the errors may be determined based on one or more of the measurements or calculated values not being within an acceptable range, or based on a combination of values indicating an error. The results of the analysis may be stored in memory at step 506, and processing may continue to step 508.

It may be desired to transmit data to the communication network (e.g., to the central processing system 12) on an occasional basis, in order to limit power consumption of the communication network device, transmission costs, and to prevent excess traffic over the communication network. Accordingly, steps 508-514 may determine when data is to be transmitted by the communication network device 122.

At step 508, it may be determined whether a warning was identified by the remote measurement device 120 or the communication network device 122. If a warning was identified, processing may continue to step 514. If a warning was not identified, processing may continue to step 510.

At step 510, it may be determined whether an error was identified by the remote measurement device 120 or the communication network device 122. If an error was identified, processing may continue to step 514. If an error was not identified, processing may continue to step 512.

At step 512, it may be determined whether it is time to transmit to the communication network. In one embodiment, the communication network device may transmit on a periodic basis. In some embodiments, the communication network device may also transmit based on some other trigger such as a request for data from the central processing system 12 or another device of a mesh network. If it is time to transmit, processing may continue to step 514. If it is not time to transmit, processing may return to step 502.

At step 514, information may be transmitted by the communication network device 122. As described herein, the information may be transmitted via any suitable communication method such as a cellular network or a wireless mesh network. The information may be transmitted according to a message format for the communication network, and may eventually be provided to the central monitoring system. Based on information received from communication network devices 122 located at fire hydrants 50 throughout the water distribution system 1, problems with the water distribution system 1 can be quickly identified and localized, and resources deployed to remedy any such problems. Once the information is transmitted at step 514, process may return to step 502.

The foregoing is merely illustrative of the principles of this disclosure and various modifications may be made by those skilled in the art without departing from the scope of this disclosure. The embodiments described herein are provided for purposes of illustration and not of limitation. Thus, this disclosure is not limited to the explicitly disclosed systems, devices, apparatuses, components, and methods, and instead includes variations to and modifications thereof, which are within the spirit of the attached claims.

The systems, devices, apparatuses, components, and methods described herein may be modified or varied to optimize the systems, devices, apparatuses, components, and methods. Moreover, it will be understood that the systems, devices, apparatuses, components, and methods may have many applications such as monitoring of liquids other than water. The disclosed subject matter should not be limited to any single embodiment described herein, but rather should be construed according to the attached claims.

What is claimed is:

1. A system to measure one or more characteristics of a liquid at a valve of a dry-barrel fire hydrant, the system comprising:
 a valve plate having a sealing surface and an exposed surface; and
 a remote measurement device integral with the valve plate, wherein the remote measurement device comprises:
  at least one sensor located at the exposed surface of the valve plate and configured to measure the one or more characteristics of the liquid; and
  a communication interface configured to transmit information representative of the one or more characteristics.

2. The system of claim 1, wherein the at least one sensor is located within one or more of a channel of the valve plate or a reservoir of the valve plate.

3. The system of claim 1, wherein the remote measurement device is at least partially located within a cavity of the valve plate.

4. The system of claim 1, wherein the remote measurement device is fixedly attached to the exterior of the exposed surface of the valve plate.

5. The system of claim 4, wherein the at least one sensor is located within one or more of a channel of the remote measurement device or a reservoir of the remote measurement device.

6. The system of claim 1, wherein the at least one sensor comprises a pressure sensor.

7. The system of claim 6, wherein the communication interface is configured to transmit a warning based on a comparison of a measured pressure by the pressure sensor and one or more thresholds.

8. The system of claim 1, further comprising a communication network device, the communication network device comprising a second communication interface configured to receive the information representative of the one or more characteristics from the communication interface.

9. The system of claim 8, wherein the communication network device is located within an upper portion of the dry-barrel fire hydrant.

10. The system of claim 8, wherein the communication interface comprises one of a wireless communication interface or a wired interface and the second communication interface comprises a corresponding one of a wireless communication interface or a wired interface.

11. The system of claim 8, further comprises:
 a wire attached to each of the communication interface and the second communication interface; and
 wherein the wire is routed between the communication interface and the second communication interface via one of an interior cavity of a valve stem of the dry-barrel fire hydrant or an interior cavity of a barrel of the dry-barrel fire hydrant.

12. A monitoring system for a fire hydrant connected to a water distribution system, the monitoring system comprising:
 a valve configured to control a flow of water through the fire hydrant, the valve comprising:
  a seat ring; and
  a valve plate assembly, the valve plate assembly being movable into contact with the seat ring to form a seal between the valve plate assembly and the seat ring to prevent the flow of water through the fire hydrant, the valve plate assembly comprising an exterior surface located opposite the seat ring and in contact with water in the fire hydrant; and
 a measuring system configured to measure at least one characteristic of water in contact with the valve, the measuring system comprising:

at least one sensor integral with the exterior surface of the valve plate assembly and configured to measure the at least one characteristic of the water; and a device communicatively coupled to the at least one sensor to receive information from the at least one sensor indicative of the measured at least one characteristic.

13. The monitoring system of claim 12, wherein the at least one sensor is located within one or more of a channel of the valve plate assembly or a reservoir of the valve plate assembly.

14. The monitoring system of claim 12, wherein the at least one sensor comprises a pressure sensor.

15. The monitoring system of claim 12, wherein the at least one sensor is configured to provide information relating to a temperature of the water.

16. The monitoring system of claim 12, wherein the device is located at a position in the fire hydrant that is opposite the exterior surface of the valve plate assembly.

17. The monitoring system of claim 16, wherein the device is located within an upper portion of the fire hydrant.

18. The monitoring system of claim 12, wherein the measuring system further comprises at least one wire connecting the at least one sensor and the device.

19. The monitoring system of claim 18, wherein the wire is routed between the at least one sensor and the device through the valve plate assembly and via one of an interior cavity of a valve stem of the fire hydrant or an interior cavity of a barrel of the fire hydrant.

20. The monitoring system of claim 12, wherein the device is configured to communicate with a central monitoring system for the water distribution system via a wireless communication network.

21. A method for measuring a one or more characteristics of a liquid at a valve of a fire hydrant, comprising:

integrating a remote measurement device with a valve plate, wherein the valve plate has a sealing surface and an exposed surface opposite the sealing surface;

sensing, with at least one sensor of the remote measurement device, one or more characteristics of the liquid;

receiving, by the remote measurement device, a signal indicative of the one or more sensed characteristics of the liquid from the at least one sensor;

transmitting, from a communication interface of the remote measurement device, information representative of the one or more sensed characteristics.

22. The method of claim 21, further comprising locating the at least one sensor within one or more of a channel of the valve plate or a reservoir of the valve plate.

23. The method of claim 21, wherein the transmitting information further includes wirelessly transmitting information to a communication network device located in the fire hydrant.

24. The method of claim 21, wherein the transmitting information further includes transmitting information to a communication network device located in the fire hydrant via a wire, wherein the wire is routed between the remote measurement device and the communication network device via one of an interior cavity of a valve stem of the fire hydrant or an interior cavity of a barrel of the fire hydrant.

* * * * *